United States Patent
Watson, Jr. et al.

(10) Patent No.: US 6,701,864 B2
(45) Date of Patent: Mar. 9, 2004

(54) RESIDUAL LIFE INDICATOR

(75) Inventors: Edgar Watson, Jr., Grayslake, IL (US); Timothy W. Caraher, Richmond, VA (US); Mindy R. Bennett, Chesterfield, VA (US); Joseph E. Roehl, Fredericksburg, VA (US); Mark J. Greenfield, Richmond, VA (US); Amber J. Ericsson, Richmond, VA (US)

(73) Assignee: Scentczar Corporation, Fredericksburg, VA (US)

( * ) Notice: Subject to any disclaimer, the term of this patent is extended or adjusted under 35 U.S.C. 154(b) by 45 days.

(21) Appl. No.: 10/261,273

(22) Filed: Sep. 30, 2002

(65) Prior Publication Data

US 2003/0127040 A1 Jul. 10, 2003

Related U.S. Application Data

(60) Provisional application No. 60/326,910, filed on Oct. 3, 2001.

(51) Int. Cl.$^7$ .............................................. G01N 21/77
(52) U.S. Cl. ......................... 116/206; 422/56; 436/169
(58) Field of Search ............................... 116/206, 207; 422/56, 86, 87, 61, 58; 436/164, 167, 169

(56) References Cited

U.S. PATENT DOCUMENTS

| | | | |
|---|---|---|---|
| 3,482,944 A | | 12/1969 | Plantz et al. |
| 3,966,440 A | * | 6/1976 | Roberts ....................... 96/117.5 |
| 4,138,216 A | * | 2/1979 | Larsson et al. ................. 422/58 |
| 4,146,887 A | | 3/1979 | Magnante |
| 4,155,358 A | | 5/1979 | McAllister et al. |
| 4,195,057 A | * | 3/1980 | Patel ............................ 422/56 |
| 4,205,043 A | | 5/1980 | Esch et al. ..................... 422/56 |
| 4,269,804 A | | 5/1981 | Kring ............................ 422/86 |
| 4,389,217 A | * | 6/1983 | Baughman et al. ............. 436/2 |
| 4,408,557 A | * | 10/1983 | Bradley et al. .............. 116/206 |
| 4,488,547 A | * | 12/1984 | Mason ................... 128/202.22 |
| 4,680,165 A | | 7/1987 | Vo-Dinh |
| 4,863,694 A | | 9/1989 | Kimmel |
| 4,913,881 A | | 4/1990 | Evers ........................... 422/56 |
| 5,045,283 A | * | 9/1991 | Patel ............................ 422/56 |
| 5,302,351 A | * | 4/1994 | Lueck ........................... 422/87 |
| 5,376,554 A | | 12/1994 | Vo-Dihn |
| 5,447,688 A | * | 9/1995 | Moore .......................... 422/56 |
| 5,602,804 A | * | 2/1997 | Haas .......................... 368/327 |
| 5,666,949 A | * | 9/1997 | Debe et al. ............. 128/202.22 |
| RE36,062 E | * | 1/1999 | Speelman et al. .......... 374/102 |
| 6,234,006 B1 | | 5/2001 | Sunshine et al. |
| 6,514,462 B1 | * | 2/2003 | Simons ................... 422/82.12 |

OTHER PUBLICATIONS

Joseph E. Roehl, Timothy W. Caraher, Kimberly A. Kalmes, Elizabeth A. Isley, "Residual Life Indicators—Point Chemical Detectors Used to Measure the Capacity of Activated Carbon in Protective Garments, Gas Mask Filters, and collective Protection Filters," Proceedings of the First Joint Conference on Point Detection for Chemical and Biological Defense, Oct. 23–27, 2000, pp. 123–130, Williamsburg, VA.

Joseph E. Roehl, Timothy W. Caraher, Kimberly A. Kalmes, Elizabeth A. Isley, "Residual Life Indicators—Point Chemical Detectors Used to Measure the Capacity of Activated Carbon in Protective Garments, Gas Mask Filters, and Collective Protection Filters," http://www.scentczar.com/residuallifeindicator/, Feb. 15, 2002.

* cited by examiner

Primary Examiner—Christopher W. Fulton
Assistant Examiner—R. Alexander Smith
(74) Attorney, Agent, or Firm—Joy L. Bryant

(57) ABSTRACT

The present invention is directed toward a residual life indicator. The residual life indicator comprises a solid, surface active, waterproof support medium having a concentric pattern imprinted thereon. The concentric pattern comprises a center pattern and at least one outer pattern. An indicator dye spot is disposed within the center pattern of the concentric patter. When the indicator dye is exposed to contaminants, the indicator dye spot visually moves toward the outer pattern.

20 Claims, 4 Drawing Sheets

RESIDUAL LIFE INDICATOR

CROSS-REFERENCE TO RELATED APPLICATIONS

This application claims the benefit of U.S. Provisional Patent Application Serial No. 60/326,910, filed Oct. 3, 2001, entitled, "Inexpensive Chemical Indicator for Volatile Organic Compounds," and is hereby incorporated by reference in its entirety.

ORIGIN OF THE INVENTION

The U.S. Government has a paid-up license in this invention and the right in limited circumstances to require the patent owner to license others on reasonable terms as provided for by the terms of Contract Nos. M67854-00-C-3045 and M67854-02-C-3000 awarded by the U.S. Marine Corps.

FIELD OF THE INVENTION

The present invention relates to an apparatus for detecting the penetration of volatile organic compounds through a material acting as a barrier. In particular, it relates to an apparatus which visually shows the residual life left in the material which is acting as a barrier.

BACKGROUND OF THE INVENTION

It is desirable to protect humans from exposure to volatile organic compounds in various work environments, such as paint booths and laboratories, where such exposure may occur. Typically, this is accomplished by having the worker wear a respirator or some other filter device while working in the environment. One such respirator is described in U.S. Pat. No. 4,155,358. This respirator is a disposable valveless chemical cartridge respirator for filtration of vinyl chloride monomer having an end of service life indicator. Of particular interest is the end of service life indicator that is provided. The indicator undergoes a dramatic and distinct color change when the cartridge has expired. The indicator comprises specially prepared activated alumina granules coated first from a 1% solution of $KMnO_4$, which is then reduced to what is believed to be $MnO_2$, and then coated from a 0.55% solution of potassium permanganate. The indicator is viewed through the side wall of the cartridge all along the edge nearest the entrance to the cartridge. The initial color is purple and upon exposure to vinyl chloride, the potassium permanganate is reduced to manganese dioxide such that there is a slow, continuous color change from the purple to brown (the color of manganese dioxide). The problem with this type of indicator is that there is no way to determine how much life is left in the cartridge based on the color change. All that is known is that the cartridge life is beginning to or has expired.

U.S. Pat. No. 4,146,887 discloses an exothermic sensor which can be fitted in the cartridge adaptor or face piece cavity of the respirator. The sensor monitors the heat evolved during adsorption of the vapor or gas into the sensor's adsorbent and triggers an alarm when the respirator cartridge has reached the end of its service life. As with the indicators described above, this sensor fails to let the user know how much life remains in the cartridge.

Other types of detection devices have also been described. In U.S. Pat. No. 4,205,043, a dosage badge for determining the exposure of firefighters to toxic gases is described. The dosage badge is affixed to the sleeve of a fireman's overcoat. This badge comprises a plurality of paper discs impregnated with a color sensitive gas indicator chemical which is mounted in alignment with apertures in a plastic substrate by a pressure sensitive tape backing. The front face of the substrate is covered with a further strip of pressure sensitive tape, which is removed to initiate indication of gas dosage by the detector. Each of the respective discs changes color in response to respective predetermined dosages of a chosen toxic gas. At low dosages, all of the discs are of a first color. As the dosage increases the colors of the indicators change. However, as with the respirator technology, this dosage badge fails to indicate how much life would be left in an adsorbent bed. Rather, the badge merely indicates the level of exposure.

Alternatively, U.S. Pat. No. 5,376,554 describes an apparatus for detecting chemical permeation of hazardous or toxic chemicals through protective clothing. The apparatus and methods utilize a spectrochemical modification technique to detect the luminescence quenching of an indicator compound which upon permeation of the chemical through the protective clothing, the indicator is exposed to the chemical, thus indicating chemical permeation. In this method, the indicator compound is analyzed for luminescence quenching after the worker has been exposed to a toxic substance. The analysis requires the use of a portable luminescence monitor. This system would not be suitable when the wearer desires to know what, if any, residual life remains in the suit or if, while wearing the suit, the protective material has been spent.

An object of the present invention is to provide a residual life indicator which, through visual indication, and not color change, identifies how much life is left in an adsorbent material.

Another object of the present invention is provide a residual life indicator which is waterproof.

SUMMARY OF THE INVENTION

The present invention is directed toward a residual life indicator. The residual life indicator comprises a solid, surface active, waterproof support medium having a concentric pattern imprinted thereon. The concentric pattern comprises a center pattern and at least one outer pattern. An indicator dye spot is disposed within the center pattern of the concentric pattern. When the indicator dye is exposed to contaminants, the indicator dye spot visually moves toward the outer pattern.

The residual life indicator of the present invention is used for identifying how much life is left in an article containing an adsorbent bed. As the indicator dye spot grows toward an outer pattern, the user is able to visually determine how much life remains in the adsorbent bed and, thus, whether the device containing the adsorbent bed is still fit for its particular use. The residual life indicator does not require the use of external readers or instruments, thus making the residual life indicator inexpensive and easy to manufacture. Moreover, because there are no color changes involved, user error, which may result from color blindness, is minimized.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF THE PREFERRED EMBODIMENTS

The present invention is for a residual life indicator. A residual life indicator is distinguished from an end of service life indicator in that the residual life indicator uses an indicator dye to predict the useful life remaining in a synthetic or natural filtering agent. Examples of such filtering agents include but are not limited to adsorbent materials such as a carbon bed or a zeolite bed that is used as a filter for water, gas masks, air, and other applications where it is desirable to filter contaminants. In contrast, an end of service life indicator typically undergoes some form of chemical change on exposure to a particular compound and fails to indicate whether or not the filtering agent has been used-up.

Figure 1:
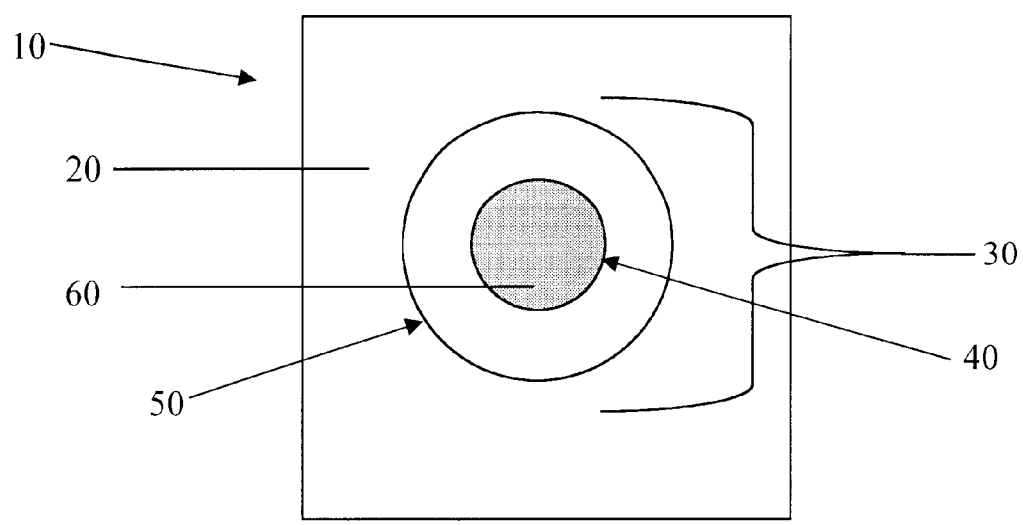
FIG. 1 is a schematic representation of a preferred embodiment of the invention.

Referring now to FIG. 1, a preferred embodiment of the invention is shown. The residual life indicator 10 comprises a solid, surface active, waterproof, support medium 20 having a concentric pattern 30 imprinted thereon. For the purpose of the present invention, it is necessary that the support medium be surface active to allow for movement of an indicator dye, solvent, and absorbed vapors along the support. In addition, it is desirable that the support be waterproof to permit use in those environments where the residual life indicator is exposed to water. In one preferred embodiment, the support is also smudge-proof. This permits ease of printing of the concentric pattern on the support. Alternatively, the support may also be washable or washable in addition to being smudge-proof. This would be desirable for applications where the residual life indicator is exposed to environments that may soil the indicator. The solid, surface active, waterproof, support medium may be prepared from any material known to those of skill in the art. Preferably, the support medium comprises a material selected from the group consisting of: a cellulose material; a synthetic material; a microglass material; and a solid support medium disposed on an inert support. Preferably, these support mediums are smudge-proof. Examples of such materials include but are not limited to a porous paper such as filter paper; a surface active material disposed on a polypropylene support; and a microglass fiber having almost no binder (similar to fiberglass). Such materials are sold under the tradenames: Whatman 40, Whatman 41, Whatman 42, Munising K-C 31333, Munising FPG-110, Munising 0525P0, Lypore 9859, Lypore 1229-B, Lypore 1251, Lypore 1378, Lypore 4453, and Lypore 6650 which are commercially available from: Fischer Scientific and Kimberly Clark. Examples of a surface active material include but are not limited to silica gel and alumina.

Figure 2:
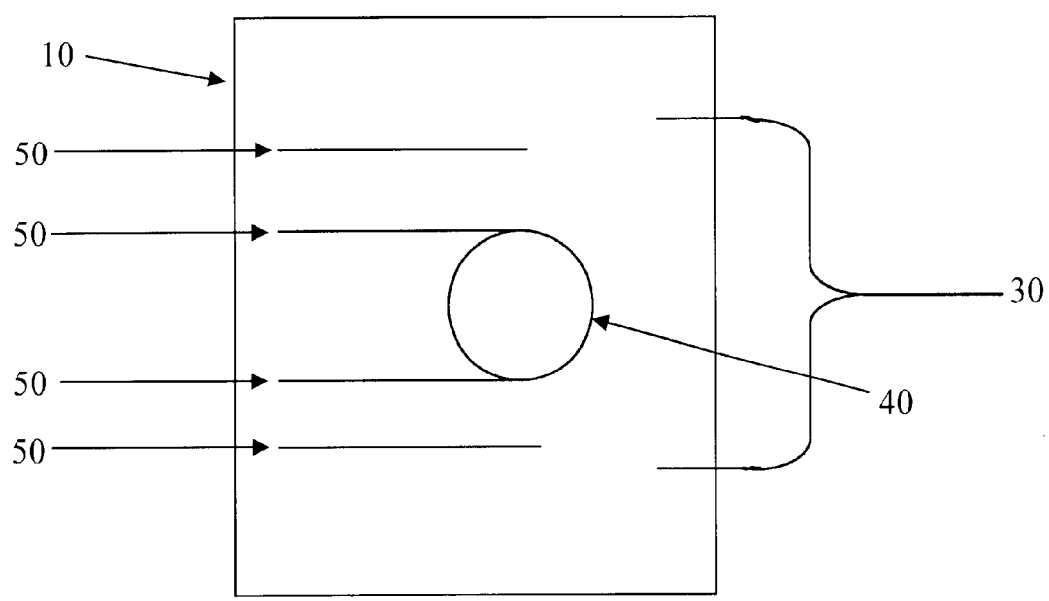
FIG. 2 depicts an alternative pattern arrangement for the present invention.

The concentric pattern 30 comprises a center pattern 40 and at least one outer pattern 50. FIG. 1 depicts the concentric pattern in its preferred embodiment of being a circular pattern, however, any concentric pattern known to those of skill in the art may be used, such as squares within squares, triangles, ellipses, or any other geometric shape. Concentric is understood to mean having a center in common. With this in mind, the concentric pattern may comprise a pattern such as that shown, which is a circle within a circle. Alternatively, FIG. 2 depicts another concentric pattern 30 wherein the center pattern 40 is a circle and the outer pattern 50 is merely a tick mark placed a particular distance away from the center. Preferably, the concentric pattern is indexed to match the residual life of an adsorbent bed. Although FIG. 1 depicts the simplest configuration which is a circle within a circle, alternatively, the concentric pattern may comprise a plurality of concentric outer patterns wherein each outer pattern is indexed to match the residual life of an adsorbent bed. This configuration allows the user to know precisely how much activity remains within the adsorbent material.

Figure 3:
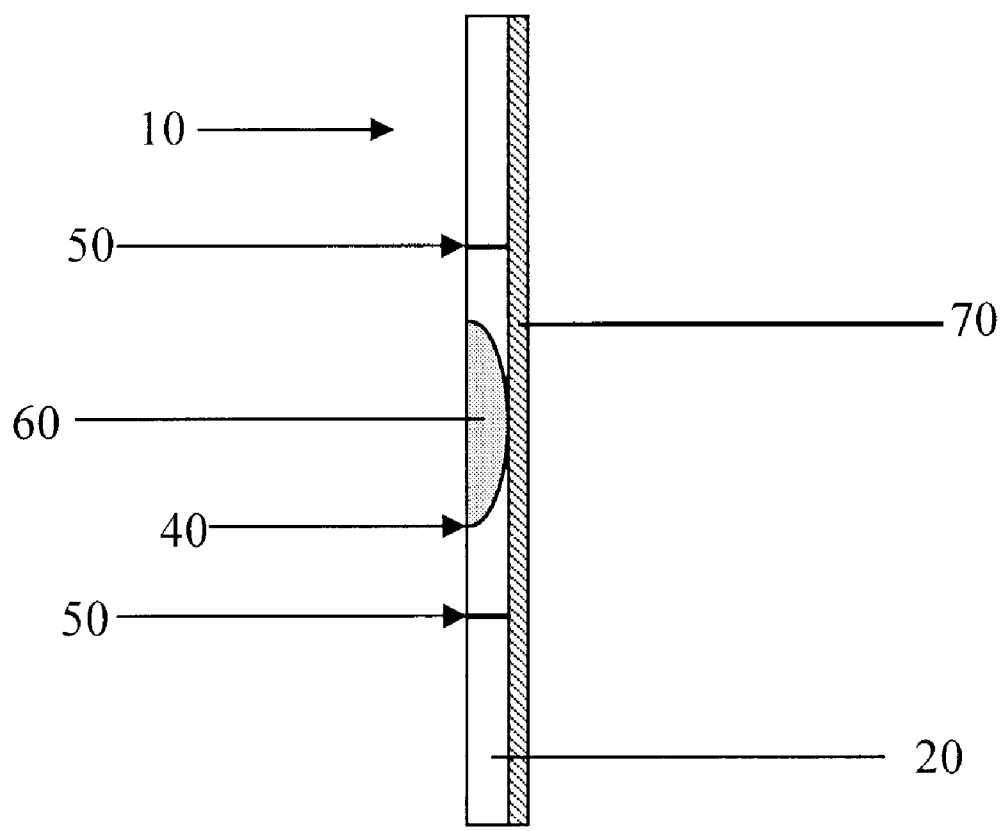
FIG. 3 is a side view of the invention depicting an alternative embodiment of the invention where a fastener is attached to the residual life indicator.

Referring back to FIG. 1, an indicator dye spot 60 is disposed within the center pattern 40 of the concentric pattern 30. When the indicator dye spot 60 is exposed to contaminants, the indicator dye spot 60 visually moves toward the outer pattern 50. Any indicator dye known to those of skill in the art may be used, selecting the indicator dye based on its reactivity to a particular organic compound to be sensed. Preferably, the indicator dye spot is sensitive to volatile organic compounds such as: petroleum-based products, jet fuel and gasoline. For the purpose of the present invention, the indicator dye spot comprises a chemical selected from the group consisting of: anthracene/anthraquione; azo/benzidine; and triarylmethine. More specifically, the anthracene/anthraquione chemical is selected from the group consisting of: Dinaphtho(1,2,3-cd: 1',2',3'-im)perylene-9,18-dione, alkyl derivative; Naphthalimide; and Dinaphtho(1,2,3-cd:3',2',1'-lm)perylene-5,10-dione, alkyl derivative. Most preferably, the anthracene/anthraquione chemical is Dinaphtho(1,2,3-cd: 1',2',3'-im)perylene-9,18-dione, alkyl derivative. Such chemicals are sold under the tradename: Fluorescent Yellow 131SC commercially available from Rhome & Haas. The azo/benzidine chemical is preferably 2-Napthalenol((phenylazo)phenol) azo alkyl derivative which is sold under the tradename Automate Red and is commercially available from Rhome & Haas. FIG. 3, depicts a further embodiment of the invention wherein a fastener 70 is disposed on a side opposite from the indicator dye spot 60. Any fastener known to those of ordinary skill in the art may be used such as an adhesive, hook and loop tape, a hook and an eye, a snap, a pin, and a safety pin. However, it is important that the substrate not be distorted (torn, stretched or puckered) by the fastener. Preferably, the fastener is an adhesive disposed on a side opposite from the indicator dye spot. Any adhesive may be used and for some applications, a pressure-sensitive adhesive may be suitable.

In a most preferred embodiment, the residual life indicator comprises a smudge-proof, waterproof, surface active, support medium disposed on a polypropylene support. The smudge-proof, waterproof, surface active support medium has a concentric pattern disposed thereon such that the concentric pattern comprises a center circle and a plurality of outer marks. Each outer mark is indexed to the residual capacity of a carbon bed. An indicator dye is disposed within the center circle. The indicator dye spot visually moves toward each outer mark when the indicator dye is exposed to known contaminants preferentially adsorbed by the carbon bed. Further, an adhesive is disposed on the polypropylene support opposite from the side having the concentric pattern and indicator dye disposed thereon.

EXAMPLE

A residual life indicator comprising a smudge-proof, waterproof, surface active, support medium disposed on a polypropylene support was prepared. The smudge-proof, waterproof, surface active support medium has a concentric pattern disposed thereon such that the concentric pattern comprises a center circle and a plurality of outer marks. Each outer mark is indexed to the residual capacity of a carbon bed. An indicator dye is disposed within the center circle. The indicator dye spot visually moves toward each outer mark when the indicator dye is exposed to known contaminants preferentially adsorbed by the carbon bed. Further, an adhesive is disposed on the polypropylene support opposite from the side having the concentric pattern and indicator dye disposed thereon.

Figure 4:
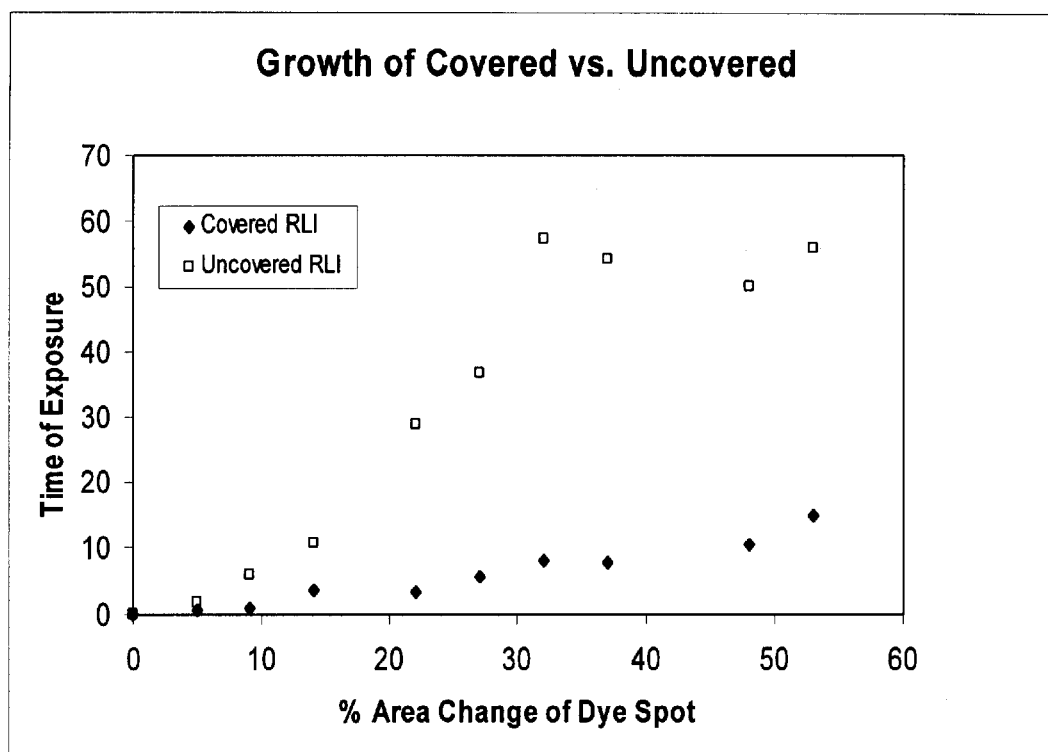
FIG. 4 is a graph showing the penetration of a carbon bed with kerosene using covered and uncovered indicators.

The residual life indicator was placed into a container with kerosene. Some of the indicators were covered with a carbon bed, and others were not. The carbon beds were analyzed for kerosene concentration. The indicators were measured before and after exposure, using a stationary digital camera to measure the percent area change. FIG. 4 is a graph depicting the test results. The Y-axis on the right is the accumulation of kerosene on the carbon bed. The X-axis on the left is the percent area change in the indicator. The open squares show the percent area change for the uncovered indicators where the closed squares show the percent area change for the covered indicators. The graph shows that the uncovered indicators grow at the same rate as the carbon bed is loading. The uncovered indicators do not start to grow significantly until after the carbon bed reaches approximately 32 hours. Thus, the indicators can accurately detect the vapors penetrating the carbon bed.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A residual life indicator for indicating the useful life remaining in a synthetic or natural filtering agent after exposure to contaminants, the residual life indicator comprising:
    a solid, surface active, waterproof, support medium having a concentric pattern imprinted thereon wherein the concentric pattern comprises a center pattern and at least one outer pattern; and
    an indicator dye disposed within the center pattern of the concentric pattern wherein the indicator dye is carried out across the solid, surface active, waterproof, support medium toward the outer pattern by the contaminants to which the indicator dye has been exposed.

2. A residual life indicator according to claim 1, wherein the solid, surface active, waterproof, support medium is smudge-proof.

3. A residual life indicator according to claim 1, wherein the solid, surface active, waterproof, support medium is washable.

4. A residual life indicator according to claim 1, wherein the solid, surface active, waterproof, support medium comprises a material selected from the group consisting of: a cellulose material; a synthetic material; a microglass material; and a solid support medium disposed on an inert support.

5. A residual life indicator according to claim 4, wherein the solid, surface active, waterproof, support medium is a filter paper.

6. A residual life indicator according to claim 4, wherein the solid, surface active, waterproof, support medium is a surface active material disposed on a polypropylene support.

7. A residual life indicator according to claim 4, wherein the solid, surface active, waterproof, support medium is smudge-proof.

8. A residual life indicator according to claim 4, wherein the concentric pattern is indexed to match the residual life of an adsorbent bed.

9. A residual life indicator according to claim 8, wherein the concentric pattern comprises a center circle and at least one outer circle.

10. A residual life indicator according to claim 1, wherein the concentric pattern comprises a center pattern and a plurality of concentric outer patterns wherein each outer pattern is indexed to match the residual life of an adsorbent bed.

11. A residual life indicator according to claim 1, wherein the indicator dye comprises a chemical selected from the group consisting of: anthracene/anthraquione; azo/benzidine; and triarylmethine.

12. A residual life indicator according to claim 11, wherein the anthracene/anthraquione chemical is selected from the group consisting of: Dinaphtho(1,2,3-cd: 1',2',3'-im)perylene-9,18-dione, alkyl derivative; Naphthalimide; and Dinaphtho(1,2,3-cd:3',2',1'-lm)perylene-5,10-dione, alkyl derivative.

13. A residual life indicator according to claim 12, wherein the anthracene/anthrquione chemical is Dinaphtho (1,2,3-cd: 1',2'3'-im)perylene-9,18-dione, alkyl derivative.

14. A residual life indicator according to claim 11, wherein the azo/benzidine chemical is a 2-Napthalenol ((phenylazo)phenol)azo alkyl derivative.

15. A residual life indicator according to claim 1, wherein the contaminants are volatile organic compounds.

16. A residual life indicator according to claim 1, wherein the solid, surface active, waterproof, support medium has a fastener disposed on a side opposite from the indicator dye.

17. A residual life indicator according to claim 16, wherein the fastener is an adhesive disposed on a side opposite from the indicator dye.

18. A residual life indicator according to claim 16, wherein the fastener is hook and loop tape.

19. A residual life indicator for indicating the useful life remaining in a synthetic or natural filtering agent after exposure to contaminants, the residual life indicator comprising:
    a solid, smudge-proof, waterproof, surface active, support medium disposed on a side of a polypropylene support wherein the solid, smudge-proof, waterproof, surface active, support medium has a concentric pattern disposed thereon, wherein the concentric pattern comprises a center circle and a plurality of outer marks, wherein each outer mark is indexed to the residual capacity of a carbon bed;
    an indicator dye disposed within the center circle, wherein the indicator dye is carried out across the solid, smudge-proof, waterproof, surface active, support medium toward the outer marks by the contaminants to which the indicator dye has been exposed; and
    a fastener disposed on a side of the polypropylene support opposite from the side having the smudge-proof, waterproof, surface active, support medium having a concentric pattern disposed thereon.

20. A process for detecting useful life remaining in a synthetic or natural filtering agent, the process comprising the steps of:
    a) providing a residual life indicator for indicating the useful life remaining in a synthetic or natural filtering agent after exposure to contaminants, the residual life indicator comprising: a solid, smudge-proof, waterproof, surface active, support medium having a concentric pattern imprinted thereon wherein the concentric pattern comprises a center pattern and at least one outer pattern; and an indicator dye disposed within the center pattern of the concentric pattern wherein the indicator dye is carried out across the solid, smudge-proof, waterproof, surface active, support medium toward the outer pattern by the contaminants to which the indicator dye has been exposed;

b) exposing the residual life indicator to organic vapors; and c) watching the indicator dye spread and move toward the outer pattern.

* * * * *